(12) United States Patent
Lykke et al.

(10) Patent No.: US 7,777,092 B2
(45) Date of Patent: Aug. 17, 2010

(54) SKIN PLATE ADHESIVE PRODUCT AND METHOD FOR ITS MANUFACTURE

(75) Inventors: Mads Lykke, Bronsheoj (DK); Frank Berg Rasmussen, Smoerum (DK); Chaabane Bougherara, Frederiksberg (DK); Carsten Sletten, Espergaerde (DK)

(73) Assignee: Coloplast A/S, Humlebaek (DK)

( * ) Notice: Subject to any disclaimer, the term of this patent is extended or adjusted under 35 U.S.C. 154(b) by 30 days.

(21) Appl. No.: 11/631,327

(22) PCT Filed: Jun. 30, 2005

(86) PCT No.: PCT/DK2005/000448

§ 371 (c)(1),
(2), (4) Date: Feb. 8, 2008

(87) PCT Pub. No.: WO2006/002634

PCT Pub. Date: Jan. 12, 2006

(65) Prior Publication Data

US 2008/0319368 A1 Dec. 25, 2008

(30) Foreign Application Priority Data

Jun. 30, 2004 (DK) ............... 2004 01039
Jul. 4, 2004 (DK) ............... 2004 01055

(51) Int. Cl.
*A61F 13/00* (2006.01)
*B32B 7/12* (2006.01)
*B44C 5/04* (2006.01)

(52) U.S. Cl. ............... 602/55; 428/343; 428/148

(58) Field of Classification Search ............... 428/40.1, 428/41.5, 41.7, 42.1, 42.3, 137, 138, 202, 428/343; 602/41, 47, 52, 57, 58, 55; 156/291
See application file for complete search history.

(56) References Cited

U.S. PATENT DOCUMENTS

| | | | |
|---|---|---|---|
| 3,073,304 A | 1/1963 | Schaar | |
| 4,367,732 A | 1/1983 | Poulsen et al. | |
| 4,867,748 A | 9/1989 | Samuelsen | |
| 5,051,259 A * | 9/1991 | Olsen et al. | 424/443 |
| 5,658,331 A | 8/1997 | Della Valle et al. | |
| 5,714,225 A * | 2/1998 | Hansen et al. | 428/114 |
| 5,965,006 A | 10/1999 | Baege et al. | |
| 6,171,594 B1 | 1/2001 | Nielsen | |
| 6,207,875 B1 | 3/2001 | Lindqvist et al. | |

(Continued)

FOREIGN PATENT DOCUMENTS

AT 392 576 B 4/1991

(Continued)

*Primary Examiner*—Patricia M Bianco
*Assistant Examiner*—Tarla R Patel
(74) *Attorney, Agent, or Firm*—Jacobson Holman PLLC (57) ABSTRACT

A skin plate product is provided, which can be better tailored with respect to controlling the properties of the first and second surfaces by cutting holes in an adhesive matrix with a laser and subsequently filling these holes with a second material. Preferably at least one zone of the second material extends from the top surface to the bottom surface of the adhesive, with an exposed part of the second material at the top surface having a different pattern than an exposed part of the second material at the bottom surface. The zones are formed as bodies of frustums of cones having their basis at the same surface.

22 Claims, 6 Drawing Sheets

U.S. PATENT DOCUMENTS

| | | |
|---|---|---|
| 6,303,700 B1 | 10/2001 | Chen |
| 6,437,038 B1 | 8/2002 | Chen |
| 6,451,883 B1 | 9/2002 | Chen et al. |
| 6,495,229 B1 * | 12/2002 | Carte et al. ............ 428/40.1 |
| 6,558,792 B1 | 5/2003 | Vaabengaard et al. |
| 6,685,683 B1 | 2/2004 | Clok et al. |
| 2004/0065232 A1 | 4/2004 | Lykke |

FOREIGN PATENT DOCUMENTS

| | | | |
|---|---|---|---|
| EP | 0 243 069 A2 | | 10/1987 |
| JP | 61113677 A | | 5/1986 |
| JP | 6065397 A | | 3/1994 |
| JP | 2003 013021 A | | 1/2003 |
| SU | 1171476 A | | 8/1985 |
| WO | WO 89/05619 | | 6/1989 |
| WO | WO 94/15562 | | 7/1994 |
| WO | WO 00/54820 | | 9/2000 |
| WO | WO 01/05340 A2 | | 1/2001 |
| WO | WO 02/066087 A1 | | 8/2002 |

* cited by examiner

SKIN PLATE ADHESIVE PRODUCT AND METHOD FOR ITS MANUFACTURE

This is a national stage of PCT/DK2005/000448 filed 30 Jun. 2005 and published in English.

FIELD OF THE INVENTION

The present invention relates to a skin plate product, more precisely a skin plate product including at least two different materials, and a method for producing such an adhesive skin plate product.

BACKGROUND

A variety of skin plate products are known which consist of or comprise a skin-friendly adhesive material which may e.g. comprise a continuous phase containing the adhesive. In these products there is often a discontinuous phase, which comprises e.g. one or more water-soluble or water-swellable hydrocolloids, starch derivatives or cellulose derivatives or hydrophilic polymers, and optionally one or more medicaments.

WO 89/05619 describes a skin plate product consisting of a matrix material and a plurality of alternating zones of a different material where at least one material is a self adhesive. In this product the zones of the second material extend through the entire thickness of the product and the zones are parallel and extend in a direction usually at right angles to the main surfaces of the product. Such a product may be produced by laminating and rolling plates or sheets of the two materials and then cutting the rolled product perpendicularly to the axis thereof.

WO 94/15562 describes a skin plate product consisting essentially of the same materials as described in WO 89/05619. According to WO 94/15562 the skin plate product comprises at least two material units being of different materials, at least one of which is a skin-friendly self-adhesive material and where a first material unit extends through the area of the entire product forming a matrix, this material unit further constituting at least a portion of the first surface and the second surface, respectively and the additional material unit or units constituting the other portion of the first and the second surface, respectively. Typically, the additional unit comprises a material which is different from the matrix material and extends somewhat into the product but not entirely through the product and the product therefore has different properties on opposite sides. These products are produced when pressing the second material into the matrix material.

Hence, the production methods described in the art are characterized by being very cumbersome and/or limiting the possible choice of materials strongly. If complex distributions of the material units or fine details are needed the production easily becomes unwieldy and exceedingly expensive. Slight changes to the design of a skin plate product usually involves time consuming replacement of major components of the production machinery or even that a different process much be used. This severely increases the cost of introducing new products and the production of small series. The inflexibility of the prior art methods strongly limits the types of skin plate products, which are technically feasible and economically viable.

SUMMARY

It is an object of the present invention to provide a skin plate product, which can be better tailored with respect to controlling the properties of the first and second surfaces. The present invention provides this by inter alia laser cut holes in a first material and subsequently filling these holes with a second material. Being able to design the exact location, orientation, distribution and/or size of the second material opens the path for adhesive products where e.g. adhesion, absorption, and permeability are controlled and balanced.

DETAILED DISCLOSURE

Thus, an embodiment of the invention relates to an adhesive with a top and bottom surface comprising a first matrix-forming material and a second material, the second material being different from the first matrix-forming material and being placed in zones comprising the second material within the first matrix-forming material, wherein at least one such zone comprising the second material extends from the top to the bottom surface of the adhesive, and wherein the exposed area of the second material at the top surface of the adhesive describes a different pattern than the exposed area of the second material at the bottom surface of the adhesive.

By different pattern is generally meant that they look different. In one embodiment the exposed area of the zone comprising the second material at the top surface of the adhesive is larger than the exposed area of the zone comprising the second material at the bottom surface of the adhesive.

In one embodiment the distribution of the exposed area of the zone comprising the second material at the top surface of the adhesive is different from the distribution of the exposed area of the zone comprising the second material at the bottom surface of the material.

In one embodiment the density of the exposed area of the zone comprising the second material at the top surface of the adhesive is different from the density of the exposed area of the zone comprising the second material at the bottom surface of the material. In one embodiment the areas of at least two neighboring holes at one of the surfaces are sufficiently large to be interconnected.

Such products provide a freedom for tailoring a skin plate product with respect to controlling the properties and the distribution thereof over the first and second surfaces of the product, which is not possible for products of the state of the art. Especially, it is easy to provide products wherein the areas of the first and second surfaces are of different size, of different distribution and/or of a different pattern.

As illustrated in the figures and examples, combinations of these embodiments are especially preferred.

The zones comprising the second material, that is the holes in the skin plate product according to the invention comprising the second material, can have varying shapes and forms. In one embodiment, the areas of the first and second surfaces are of different size on the surfaces of the skin plate product. Moreover, the area of the zones comprising the second material on the first surface (the top surface) and the area on the second surface are preferably of any arbitrary shape such as irregular or regular shape such as in the shape of a rectangle, square, triangle, star, parallelogram, rhomb, ellipse, circle, super-ellipse or super-circle.

According to a preferred embodiment of the invention at least one of the holes does not intersect at least one of the surfaces. In this way different areas are obtained on one surface of the skin plate product compared to the other surface of the skin plate product.

In an another embodiment the second material is in the form of cylindrical bodies having their axes essentially perpendicular to the planes of the first and second surfaces and at least one of the cylinders has a length shorter than the thickness of the skin plate product.

This is an alternative way to provide different areas of the zone on one surface of the skin plate product compared to the other surface of the skin plate product.

According to a preferred embodiment of the invention, the second material is in the form of bodies of frustum of cones. This is an alternative way to provide a product with different areas on one surface of the skin plate product compared to the other surface of the skin plate product. The cones can be arranged in any fashion e.g. where the basis of the cones is positioned alternating on the first and the second surface of the skin plate product or e.g. where a majority of the cones have their basis on one side of the product. It is also possible that all the cones have their basis at the same surface. In these embodiments the areas of the cone shaped holes in the first and the second surface are not only different but furthermore some of the cones may only be present on one side of the product. Hence, different properties are obtained on the first and the second surface of the product.

Furthermore, using slanting angles, the boundary surface between the holes and the first matrix-forming material can vary, giving the holes an irregular shape.

According to yet another preferred embodiment of the invention, the second material is in the form of cylindrical bodies having slanting axes in relation to the planes of the first and second surfaces and at least one of the cylindrical bodies has a length insufficient to reach from one surface of the product to the other surface.

The axes of the slanting cylindrical bodies can be arranged in a parallel or non-parallel fashion.

According to another preferred embodiment of the invention, the boundary surface between holes and the first matrix-forming material is in the form of a surface which intersects the first and second surfaces in slanting angles (referred to as the angle alpha in the figures). Hence, the areas of the first and second surfaces constituted by the second material can have arbitrary shapes which are differently distributed.

When the second material is in the form of cylindrical bodies having slanting axes in relation to the plane of the first and the second surfaces, the areas of the holes on the surfaces are at different locations on each side of the product. Therefore, it is possible to e.g. focus the properties of the materials in the holes on a specific location on one side of the skin plate product, but maintaining an even distribution of the holes on the other side of the product. This will result in the possibility of controlling the properties of the skin plate product optimally.

It is also foreseen that the holes may have at least a symmetrical plane to at least one of the first or second surfaces. Another option is that there is a symmetrical axis through the centre of the area of the first or second surface constituted by the second material and the holes will obtain the shape of e.g. a cylinder, pyramid or a cone.

Furthermore, in another embodiment of a skin plate product according to the invention it is possible that all of the holes for taking up a second material extend through the entire thickness of the product. In this embodiment of a skin plate product the slanting angle of the boundary surface between the second material and the first matrix-forming material can vary as described above. Accordingly, the holes may have an irregular shape.

When the holes have a conical or a pyramidal shape the materials in the holes can have a bigger effect on one side of the skin plate product compared to the other side of the product as the holes cover a different sized area on the surfaces. This could for example be used to control the peeling force of the skin plate products from the skin, and also to provide different peeling force in different directions for reducing the risk of unintended removal of the product during use and facilitating in tended removal of the product.

According to yet another preferred embodiment of the invention, the areas of at least two neighbouring holes at one of the surfaces are sufficiently large to be interconnected.

In this case the interconnected part of the holes can form a unit of a second material which can be made out of a material which has large absorbing capacity. In a skin plate product where the first matrix-forming material is made out of skin-friendly adhesive, it is possible to obtain a skin plate product where one side of the product has good adhesive properties and also provides a high capacity of transporting large amounts of fluid from the skin surface. In this type of a skin plate product, such units may serve as a reservoir and may even be exchanged with another unit of the same material without requiring that the skin plate product be removed (see e.g. FIG. 3).

A skin plate product where some of the holes are interconnected essentially forming a pad on one side of the product can be advantageous in highly exudative wounds. The many holes on one side of the product will then function as multiple channels that draw liquid from the wound to the pad on the other side of the product which is capable of containing a large amount of liquid. This pad can optionally be replaced with another similar pad when the first pad is saturated. Thereby, the whole dressing on the wound does not need to be replaced.

In a typical embodiment of the invention the ratio between amount (weight) of first matrix forming material and the second material is in the range of 60:40 to 80:20. Presently, a ratio over 40:60 (that is 60% of the second material) is hard to imagine. On the other extreme, however, often dots of second material with active compounds are requested giving a ratio of 199:1 (0.5% second material).

In one embodiment of the invention, a skin plate product has at least one of the holes not completely filled. Accordingly, one surface of the skin plate product is flat while the other surface is provided with indentations. Thus, it is rendered possible to use a second material made out of a swellable material which swells up and fills the hole after absorbing fluid without increasing the total thickness of the product which will be advantageous when the skin plate product is covered with a material hampering a free expansion, e.g. a shoe or a belt—or even a liner.

The skin plate product according to the invention preferably comprises two or more different materials, at least one of the materials being a skin-friendly adhesive.

The skin-friendly adhesive may be of any kind, e.g. an acrylic adhesive, a hydrogel adhesive or a hydrocolloid adhesive. The adhesive material may e.g. comprise caoutchouc, caoutchouc-like synthetic homo-, co- or block-copolymers, polyacrylate and copolymerisates thereof, polyurethane, silicone, PPO, Akrylat blockcopolymer polyisobutylene, polyvinyl ether and natural or synthetic resins or mixtures thereof optionally containing zinc oxide. The adhesive matrix may further contain various additives, such as plasticizers, thickeners and others, and optionally hydrocolloids and/or various medicaments, such as antiseptics, hormones, nicotine etc.

Skin-friendly adhesive may suitably be a medical grade barrier adhesive known in the art such as the formulation being disclosed, for example in U.S. Pat. Nos. 4,367,732, 5,051,259, 5,714,225, 6,171,594, 6,303,700, 6,451,883 or 6,437,038, or in WO Applications Nos. 00/54820, or 01/05340.

Furthermore one or more of the materials, provided they do not get into contact with the skin in use, may consist of a non-skin-friendly adhesive material.

In a preferred embodiment the first matrix-forming material is a soft, hydrophobic adhesive, which is very skin-friendly and has a very high resistance towards erosion by water. Examples of such materials are SIS/SI gels, Silicone gels, PPO gels, Acrylic block copolymer gels, and PU gels. The second material is then chosen according to its purpose such as absorption of water, release of a biologically active substance or other. According to the invention a large freedom in the pattern of the holes in the matrix-forming material is provided. Hence, there are not necessarily special requirements to the adhesive properties or the erosion resistance of the second material.

In another preferred embodiment the first matrix-forming material comprises a pressure sensitive adhesive composition such as those described or referred to in WO 89/05619 or WO 94/15562. The first matrix-forming material may even be a skin plate product as disclosed in the prior art and comprising more than one pressure sensitive adhesive composition. Holes made in the matrix-forming material according to the invention are then filled with a second material serving special purposes, which cannot readily be fulfilled in a formulation where the second material constitutes a part of the matrix material.

Special purposes include e.g. release of biologically active substances and sensory materials such as materials sensitive to humidity, pH, specific elements or compounds (inorganic or organic) or other. Other possibilities include materials having conducting properties (heat, current, ions), materials having barrier properties, materials required for further processing such as welding (including laser welding) or surface treatment. The second material may also provide a suitable environment for an electronic or optical component or device.

Different skin plate products can easily be made according to the method of the invention, where the formation of the holes and the combination of materials can be adjusted as desired.

A large number of other materials may be incorporated in the product according to the invention, either as independent units or as portions of materials or units. An example hereof is that one or more types of materials or units may consist of a foam material with open or closed cells. The foam material may contain a biologically active substance, e.g. a medicament or an antiseptic or antibiotic. The biologically active substance may be present in the cells of a foam with open cells, or be present in the foam material itself, that is in the walls of open or closed cells which may e.g. consist of a foamed gel material, such as gelatin.

Biologically active substances may also be present in other materials than foam materials E.g. one or more material units may be built from a hydrophilic gel material containing an agent effective against warts, e.g. cantharidine, salicylic acid, silver nitrate, podophyllin or an anti-metabolical cystostatic, such as cytarabine, fluorouracil or mercapto-purine.

One or more materials or units may be built from a hydrophilic gel material including one or more keratolytically active substances, e.g. carbamide, salicylic acid and/or lactic acid.

Further, one or more materials or units may contain one or more compounds impeding mitosis, e.g. anthracene, silver nitrate or glucocorticoids, such as mildly, medium strongly or strongly active corticosteroids, such as hydrocortisone, triamcinolone acetonide or betametasone.

One or more of the materials or units as mentioned above be gels with adhesive properties, or they may be gels devoid of adhesive properties. Such gel materials may be hydrophilic or hydrophobic, optionally of a desired HL-balance (hydrophilic-lipophilic balance), and optionally a supporting structure may be incorporated therein in the form of a foam of e.g. polyether, collagen or gelatin, or in the form of fibres, filaments or woven or non-woven textile material, e.g. of polyester or cotton. Hydrophilic gels may e.g. be mixtures of karaya and glycerol; of pectin, comparatively low-molecular polyethylene glycol and glycerol; or mixtures of gelatin, glycerol and water.

Hydrophobic gels may e.g. consist of mixtures of styrene-isoprene-styrene block copolymer and liquid paraffin; mixtures of styrene-isoprene-styrene block copolymer, liquid paraffin and dioctyladipate; or mixtures of nitrocellulose, ricinus oil and rosin.

As examples of active substances which may be incorporated into the gel materials may further be mentioned antiseptics, such as iodophors, silver compounds, hexidine or chlorohexamine, vitamins and antibiotics, wound-healing agents and growth-promoting substances, such as growth hormone.

Foam materials which may be present as a special kind of material unit or form a supporting structure in the gel materials just mentioned, may e.g. be of polyether, polyethylene, polyvinyl chloride, polyurethanes, gelatin or collagen.

One or more of the materials or units may further consist of or contain alginate, e.g. in the form of a fibrous and/or porous alginate pad, preferably containing a mixture of sodium alginate and calcium alginate. Mention of such alginate materials can e.g. be found in EP patent application No. 243 069 or in SU certificate No. 1 171 476.

The skin plate product may also incorporate one or more material units with so-called super absorbing materials. These are well-known in connection with absorption products, such as sanitary towels and diapers.

The product according to the invention may be circular, oval, square or rectangular or have any other embodiment. For use in ostomy equipment the product produced according to the invention may e.g. have a central aperture.

Adhesive surfaces are preferably protected by a protective cover or a releasable liner until use. A protective cover or releasable liner may for instance be siliconized paper. It does not need to have the same contour as the product, e.g. a number of products may be attached to a larger sheet of protective cover. The protective cover is not present during the use of the product of the invention and is therefore not an essential part of the invention.

Furthermore, the edge of the product may be bevelled as disclosed in U.S. Pat. No. 4,867,748.

The skin plate product may comprise a top layer, such as a film, a non-woven layer or a foam. The top layer is preferably flexible and conformable top layer and an adhesive layer covering at least the edge portion of the skin contacting surface of the top layer. An absorbent element may be located at the central part of the coated top layer leaving parts of the adhesive coated top layer as a discontinuous flange surrounding the absorbent element.

The top layer of the dressing according to the invention may be any layer, such as a polyurethane film, foam or non-woven or combination of films or layers which, in combination with the adhesive, shows the desired characteristics of the dressing according to the invention. The film may e.g. be produced from a polyolefin material, polyurethane material or polyethylene.

The top layer is preferably permeable to vapour but impermeable to water. In another embodiment, where moisture from the back-side is to be avoided, it is preferred to have en impermeable backing.

A preferred material for the top layer may be polyurethane. The top layer is partly or fully covered with an adhesive. The coating may be in the form of a pattern or e.g. only situated on the flange.

In a further aspect, the invention relates to an ostomy appliance comprising a skin plate of the invention as a part of or all of an adhesive wafer for adhering such ostomy appliance to the skin. Such ostomy appliances may, apart from the skin plate product, of the invention be of a kind known per se and may be made in analogy with products in the art. Such ostomy appliances may be one-piece appliances or a body side member which together with an exchangeable collecting member forms a conventional two-piece appliance.

In a still further aspect the invention relates to a wound dressing comprising a skin plate product of the invention as a part of or all of an adhesive surface for adhering such wound dressing to the skin.

In a further embodiment of the invention the second material is constituted by units of at least two second materials. The two units of the second material are of two different materials and can have different properties which are suitable for the product of the invention. This could e.g. be the case where one of the units is a sensor. The sensor would then appropriately be placed together with another unit of second material which has properties that supports the function of the sensor. An example of this case is the use of e.g. a humidity sensor unit, a pH sensor unit or a sensor based on electronics.

The invention also relates to a method of producing a skin plate product for use as a semi-manufacture comprising the steps of:
a) providing a first matrix-forming material
b) forming holes in the matrix-forming material by removing material corresponding to the desired pattern of the second material
c) providing a source of at least the second material and dispensing the same into the voids provided by removing material in step b).

Preferably, the first material is a continuous source of a skin-friendly material.

According to the invention it is possible by first providing holes in the first matrix-forming material and thereafter fully or partly filling the holes with one or more materials to easily produce a skin plate product with surfaces having different properties.

The production of these products is very flexible. The invention even allows the production of skin plate products as described in WO 89/05619 using materials, which are too soft to be cut, or products as described in WO 94/15562 where the second material is softer than the first matrix-forming material. The present invention also provides a way to produce products described in WO 94/15562 without the flow of mass of the first matrix-forming material, which may have an adverse effect on the physical properties of the final product.

According to the method of the invention the material of the first matrix-forming material being removed in step b) can be removed by mechanical means e.g. by using punching machines, drills or pins. However, it is preferred to use a contact free method such as radiation-, hot air-, or water jet technology. This provides for a much less expensive production of skin plate products compared to the methods described in the art as complicated procedures to avoid deposition of adhesive residues on the equipment are avoided.

Especially preferred is the use of laser technology for materials removal. Lasers of a wide variety can be used including continuous and pulsed $CO_2$-, diode-, Nd:YAG- and Excimer lasers. Lasers are relatively inexpensive, easily integrated into production lines and allow for a very quick and inexpensive change from one pattern to another simply by changing the programming. Very complex patterns with high precision and fine details can be made using a laser with very little extra effort and without making the production considerably more expensive. Furthermore, lasers provide an easy control of the shape and depth of holes, allow holes to be made on both surfaces of the product and can provide secondary structures on a skin plate product after forming a primary structure, e.g. the holes.

Many of these advantages are, to a certain extent, also obtained using other contact free technologies.

The holes can be filled e.g. by applying the second material on the surface of the matrix material and thereafter pressing the material into the holes e.g. using a doctor blade or rolling a cylinder over the surface. This process can be repeated several times as required. Contrary to prior art the additional materials do not need to be more firm than the first matrix-forming material.

According to a preferred embodiment of the method of the invention the holes formed in the first matrix-forming material can be filled with two different materials.

To avoid spreading the second material onto the surface of the first matrix-forming material and not only into the holes, the matrix-forming material can initially be covered with a removable layer, liner or film. Thus when forming the holes the removable layer will obtain the same pattern of holes as the first matrix-forming material, and when pressing the second material into the holes, the removable layer functions as a mask which can be removed afterwards.

One of the materials placed in the holes can be a sensor, which appropriately can be placed in the holes using e.g. robots.

Holes are preferably made without turning or tilting the first matrix-forming adhesive during the process. Hence, holes with slanting angles are preferably made using laser technology but can be made using other technologies although with higher process complexity.

Immediately before or during the final filling of the holes it may further be expedient to subject the product to light heating and/or pass it through calibration rollers to ensure that the material units cohere sufficiently and have plane surfaces. It may also be necessary to let the final product set for some time to ensure a sufficient cohesion of the materials contained in the holes.

This procedure allows a high degree of flexibility in the chose of materials without being limited to materials sufficiently pliable when laminating and rolling and which are rendered sufficiently hard before cutting, typically by cooling. Also, it is not needed that the material of the second unit must be considerably harder than the material of the first unit, nor that the first material unit must be relatively plastically deformable during the manufacturing of the product in order to allow an easy pressing of the second material into the first unit causing a considerable flow of mass of the material of the first unit.

Finally, the present production methods is flexible and can be adjusted easily without the need for purchase and installation of specialized equipment.

One aspect of the present invention relates to a skin plate product having a first and a second surface and comprising a first matrix-forming material provided with a number of holes extending from at least one surface of the product, said holes containing at least one second material which is different from the matrix-forming material and wherein at least one of the materials is a skin-friendly adhesive material, wherein a plurality of the holes extend from the first to the second surface and wherein areas of the first and second surfaces corresponding to the holes and being constituted by the second material are of different size.

Another, related, aspect of the invention relates to a skin plate product having a first and a second surface and comprising a first matrix-forming material provided with a number of holes extending from at least one surface of the product, said holes containing at least one second material which is different from the matrix-forming material and wherein at least one of the materials is a skin-friendly adhesive material, characterized in that a plurality of the holes extend from the first to the second surface and that areas of the first and second surfaces corresponding to the holes are differently distributed.

Related to these embodiments is the embodiment wherein all of the holes for taking up a second material extend through the entire thickness of the product and wherein the boundary surfaces between holes and the first matrix-forming material are in the form of surfaces which intersect the first and second surfaces in varying slanting angles.

Another aspect of the invention relates to a method for producing such a skin plate product in which holes are formed in a first material and hereafter an additional material is dispensed into the holes.

Still further, an aspect of the invention relates to an ostomy appliance comprising a skin plate product of the invention.

Yet further, the invention relates to a wound dressing comprising a skin plate product of the invention.

In a typical embodiment of the invention, the product is manufactured by providing holes in the first material and then filling the holes with the second material. Such holes, being the zones comprising the second material within the first matrix forming material thus constitute unoccupied spaces, or depressions hollowed out of the first material. This shall been seen in the light of e.g. hydrocolloid containing adhesives, where the hydrocolloids are mixed into the first material.

Often the term "hole" as described in the invention relates to depressions extending somewhat into the matrix material or passages extending from one side of the product to the other side of the product. Thus, the hole or the zone comprising the second material, will typically extend from one surface of the adhesive to the other, despite that the hole might not be filled completely.

Holes are preferably made without turning or tilting the first matrix-forming adhesive during the process. Hence, holes with slanting angles are preferably made using laser technology but can be made using other technologies although with higher process complexity.

When using the terms "top" and "bottom" surface of the adhesive, those are meant as relative terms, not describing an actual top or bottom surface.

A skin plate product according to the invention may be used for securing ostomy appliances to the skin and for sealing around an ostomy, for securing wound dressings or wound drainage bandages to the skin, for securing devices for collecting urine to the skin, or for securing orthoses or prostheses to the skin.

A preferred embodiment relates to an ostomy appliance comprising a skin plate product of the invention as a part of or all of an adhesive wafer for adhering such ostomy appliance to the skin.

Another preferred embodiment relates to a wound dressing comprising a skin plate product of the invention as a part of or all of an adhesive surface for adhering such wound dressing to the skin.

The invention will now be further described with reference to the drawings.

DETAILED DESCRIPTION OF THE DRAWINGS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
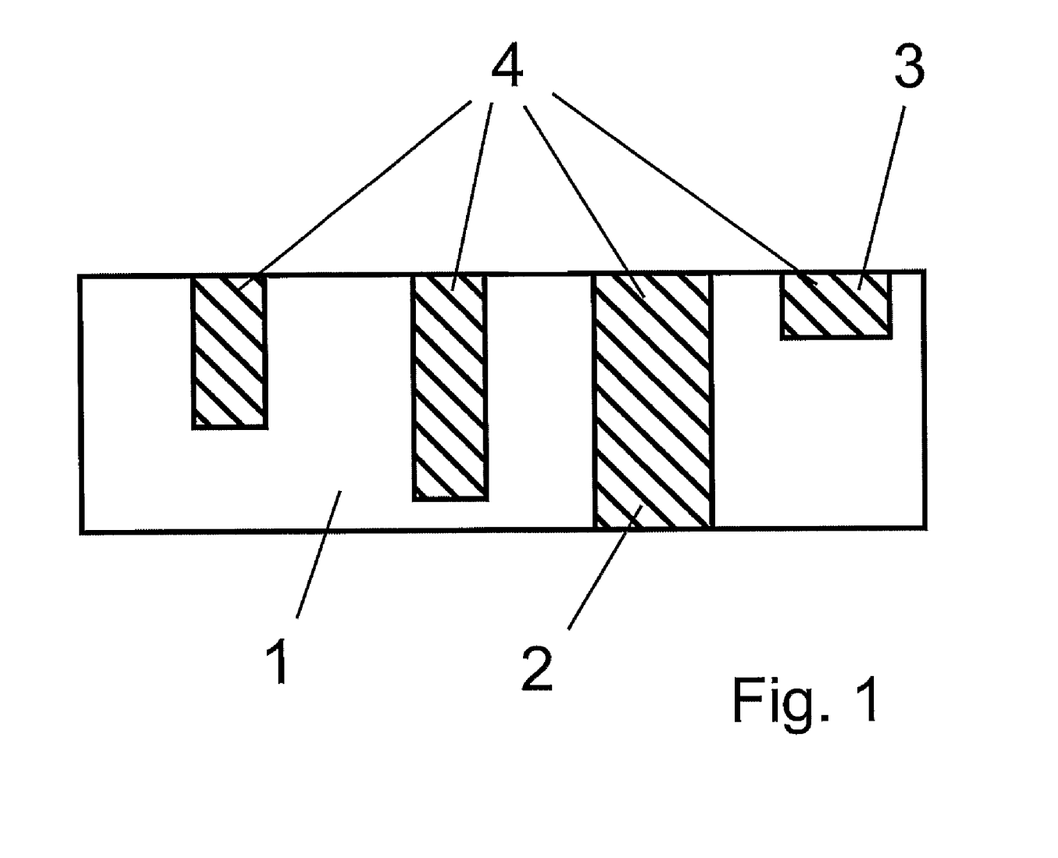
FIG. 1 shows a cross-sectional view of a skin plate product in accordance with the present invention.

FIG. 1 shows a cross-sectional view of a skin plate product having a matrix material (1) intersected by a plurality of holes (2, 3) and the holes are filled up with a second material (4, hatched). The holes do not have the same length, i.e. some of the holes (2) extend from one surface of the product to the other surface, while other holes (3) only extend somewhat into the matrix-forming material (1). The matrix material (1) and the second material 4 are different from each other.

Such a product provides a way to vary e.g. the absorption capacity over the surface facing the skin of a skin plate product simply by varying the volume of the second material responsible for the absorption in contact with the skin. A large absorption capacity can be obtained where the filled holes extend from one surface to the other and an absorbing pad is placed on top of the adhesive skin plate, a small absorption capacity is obtained where the filled holes only extend somewhat into the first matrix-forming material.

The embodiment of FIG. 1 is also preferred for a skin plate product where both surfaces have identical material configurations except where other components (foils, couplings etc) are to be attached to one of the surfaces. Such a product is obtained if most holes extend through the skin plate product except where components are to be attached, where the holes only extend from the surface not used for attachment and somewhat into the material.

Similar products can be obtained if the distribution of the holes is different on the two sides of the product. It may e.g. be possible to concentrate the areas of the second material on part of the surface in contact with the skin to obtain e.g. a higher absorption capacity in that part.

Figure 2:
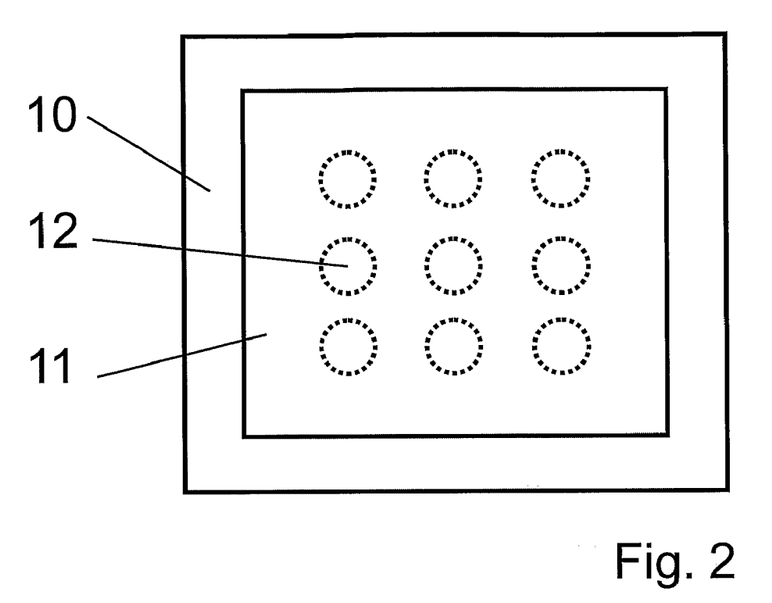
FIG. 2 shows a top view of a skin plate product in accordance with the present invention.

FIG. 2 shows a top view of a skin plate product comprising a matrix-forming material (10) and a third material (11, hatched) which covers a large area on the surface of the matrix-forming material (10). A plurality of holes (12) are contained in the matrix-forming material (10) under the third material (11) are shown with a dotted line. The holes contain a second material, however the second material can be the same material as the third material (11).

Figure 3:
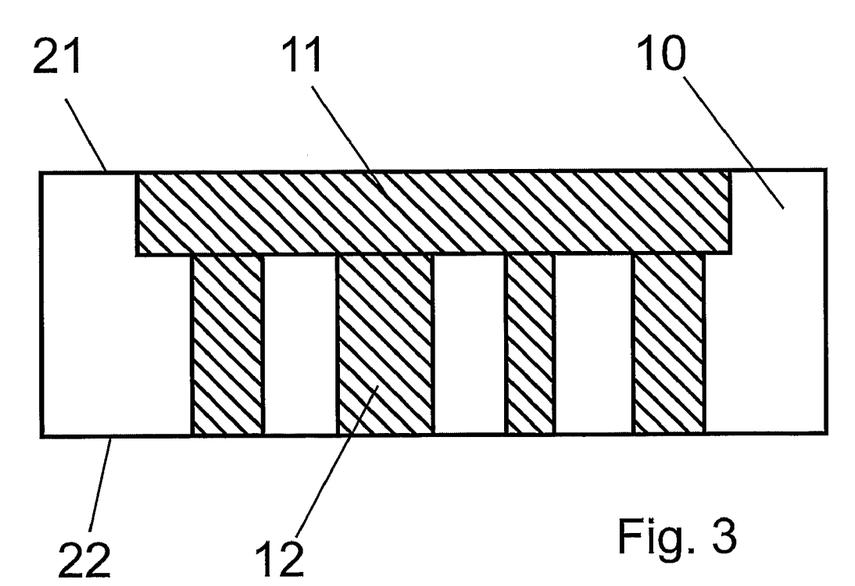
FIG. 3 shows a cross-sectional view of the skin plate product shown in FIG. 2.

FIG. 3 shows a cross-sectional view of the skin plate product shown in FIG. 2. The matrix-forming material (10) is intersected by a plurality of holes (12), which contain a second material. However, the holes through the matrix material (10) are connected on one side of the product (21) in essentially a single hole (11) on the surface, possibly more than one hole, but fewer holes than on the surface of the other side of the product (22). The larger hole (11) is filled with a third material, however the third material can also be the same as the second material.

An adhesive construction as shown in FIG. 3 is preferably made by the steps of
a) Making a 0.4 mm indentation of size 50×50 mm into matrix material B as described in example 9;
b) Making 9 additional holes through the matrix material within the indented area as described in example 8
c) Filling the holes with hole material I or II as described in example 8

Figure 4:
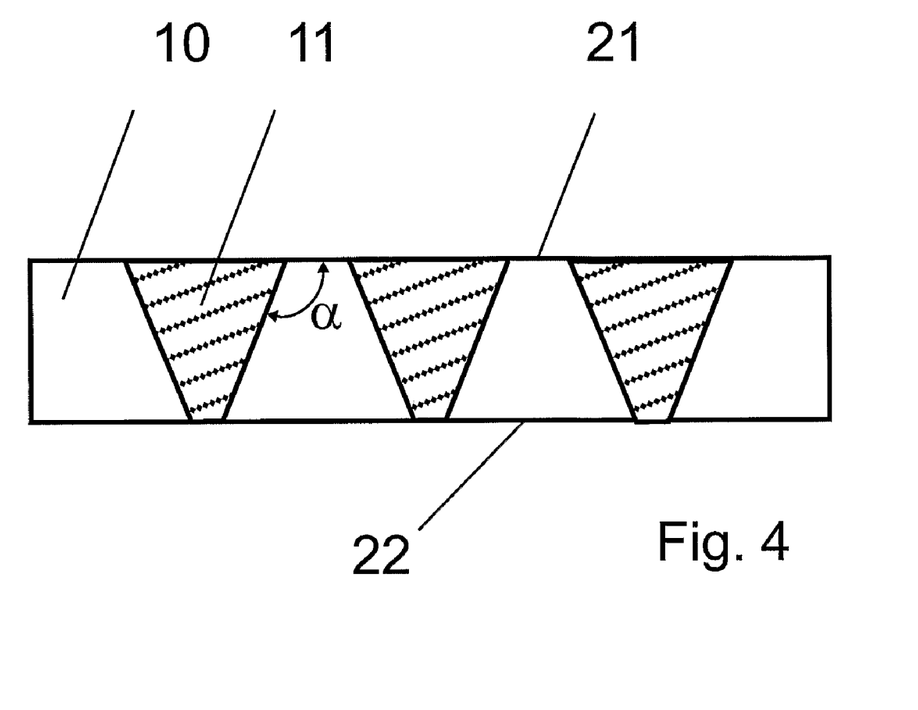
FIG. 4 shows a cross-sectional view of another skin plate product in accordance with the present invention.

FIG. 4 shows a cross-sectional view of a skin plate product with a matrix-forming material (10) intersected by a plurality of holes (11). Zones (11) cover different areas on faces (21) and (22) but extend though the entire thickness of material (10); thus, total area of the holes on the top surface (21) is larger than the total area of the holes on the bottom surface (22). The angle between the top surface and the slanting angles of the zone of the second material is referred to as alpha ($\alpha$).

Figure 5:
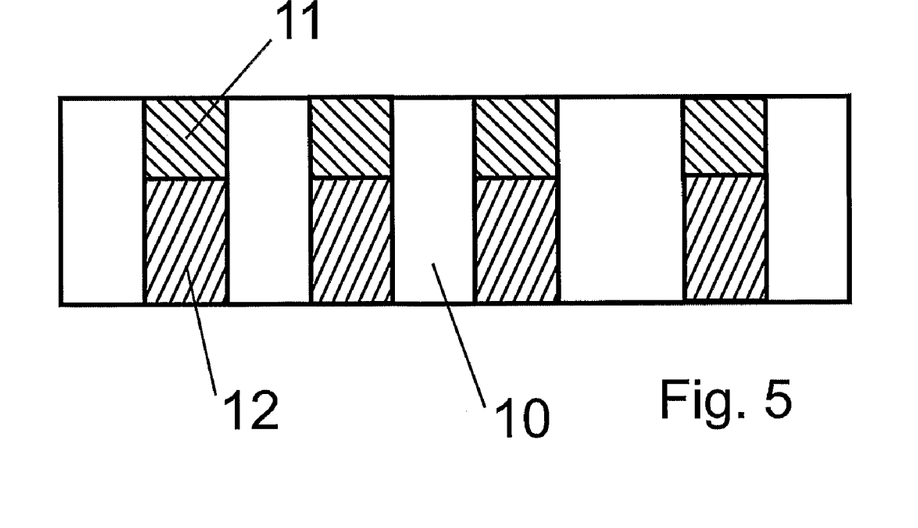
FIG. 5 shows a cross-sectional view of yet another skin plate product in accordance with the present invention.

FIG. 5 shows a cross-sectional view of a skin plate product according to the invention where holes in the matrix-forming material (10) extend from one surface to the other surface and are filled with a second material (11) on one side of the product and a different third material (12) on the other. Note that materials (11) and (12) are different but are considered as one zone. This one zone (the zones comprising the second material) extend trough the entire thickness of the product.

In this preferred embodiment, the surface areas constituted by the second material are different on the two faces of the product; that is, the surface area of the second material on one side of the product is zero. This feature is beneficial if the second material provides body fluid absorption capacity but little adhesion to skin. In this case it may be of value to reduce the area of the second material in contact with the skin but still have sufficient volume of the second material to ensure absorption capacity.

Similarly, the second material may have release properties (of a biologically active substance) but have low adhesion or absorption properties. Again it may be important to reduce the area of the second material in contact with the skin without reducing the volume of the second material.

Alternatively, if the second material has low cohesion but provides good adhesion, high absorption, efficient release of an active substance, or is particularly skin-friendly it may be useful to have a large area of the second material facing the skin without increasing the volume of the second material.

The product can be produced by firstly making holes in the matrix-forming material e.g. by using laser-drilling, thereafter applying the second material (11) onto the surface of the matrix-forming material (10) and rolling over the surface so that the second material will be displaced in to the holes. The amount of second material in the holes depends on the amount of second material applied to the surface of the matrix-forming material. The third material (12) can be applied in the same or similar manner as the second material (11).

Figure 6:
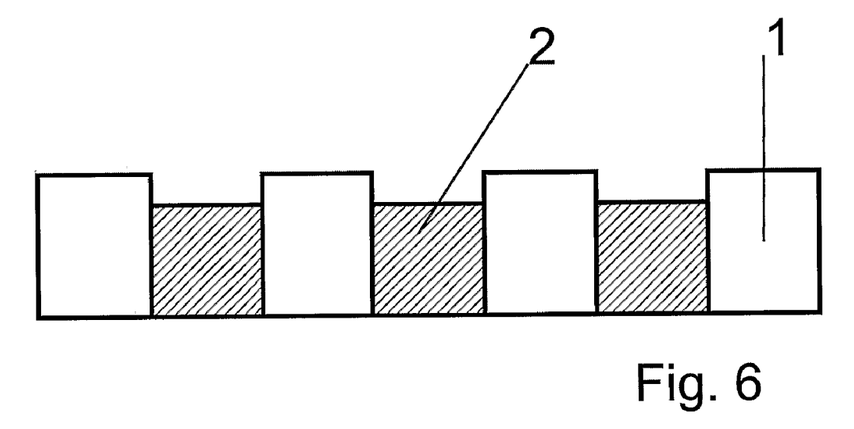
FIG. 6 shows a cross-sectional view of still another skin plate product in accordance with the present invention.

FIG. 6 shows a skin plate product comprising a matrix-forming material (1) intersected by a plurality of holes, where the holes contain a second material (2). The second material (2) does not fill the whole volume of the holes (1) leaving a pocket of air in the top of the holes. Thus, the skin plate product shown in this figure is not completely flat. This embodiment is particularly advantageous where the second material (2) is a swellable material. When swelling during use, this second material will gradually fill the left over space.

If the second material swells due to absorption of body fluids or water this has much less consequence for the first matrix-forming material, which in the prior art products must be able to follow the thickness increase of the second material.

Figure 7:
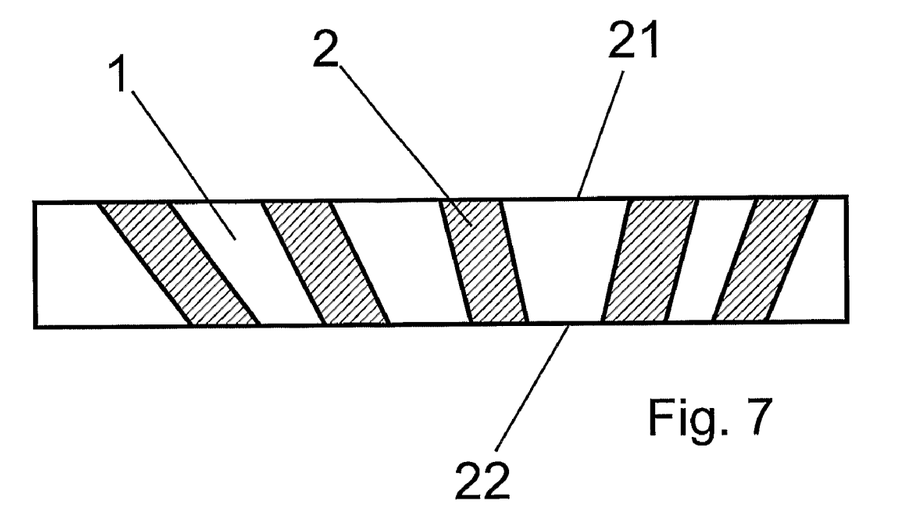
FIG. 7 shows a cross-sectional view of another skin plate product in accordance with the present invention.

FIG. 7 shows a cross-sectional view of a skin plate product with a matrix-forming material (1), intersected by a plurality of holes, all extending from one surface (21) of the product to the other surface (22). The holes are in the form of cylindrical bodies having slanting axes in relation to the planes of the first (21) and second (22) surfaces. In this embodiment the axes of the slanting cylindrical bodies are not parallel, such that the exposed area of the second material at the top surface (21) describes a different pattern than the exposed area of the second material at the bottom surface (22).

Figure 8:
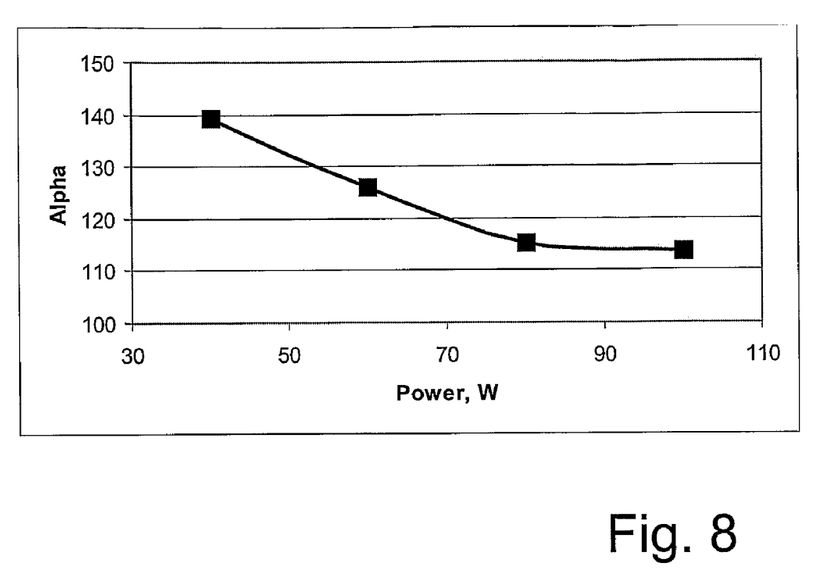
FIG. 8 is a graph of the creation of holes having a conical shape for a skin plate product in accordance with the present invention.
Figure 9:
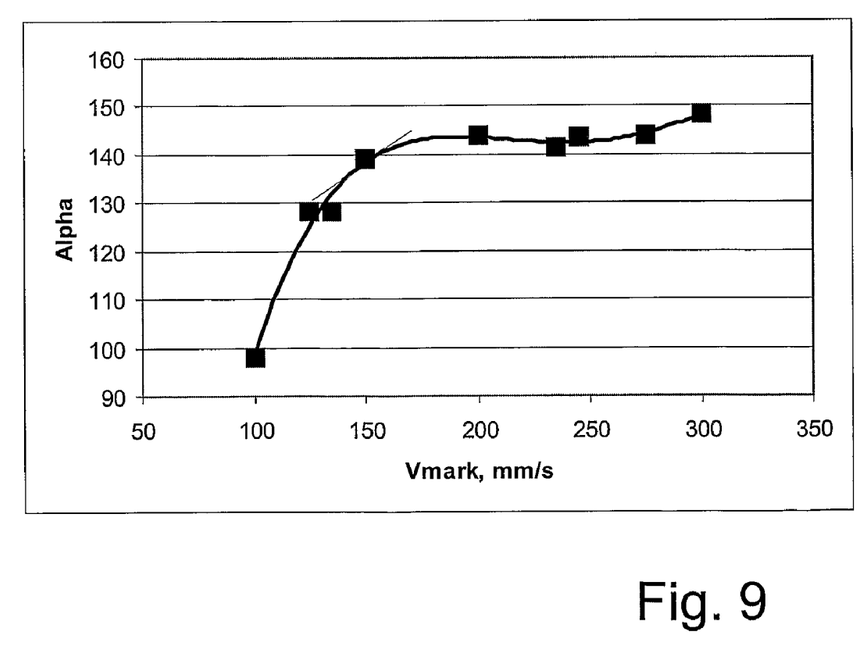
FIG. 9 is another graph of the creation of holes having a conical shape for a skin plate product in accordance with the present invention.

FIGS. 8 and 9 illustrate the creation of holes with a conical shape. The largest diameter is 4 mm and the angle alpha ($\alpha$) (see FIG. 4) is varied by tuning the laser power (FIG. 8) or the mark velocity (FIG. 9). The other parameters are as in example 8.

Figure 10:
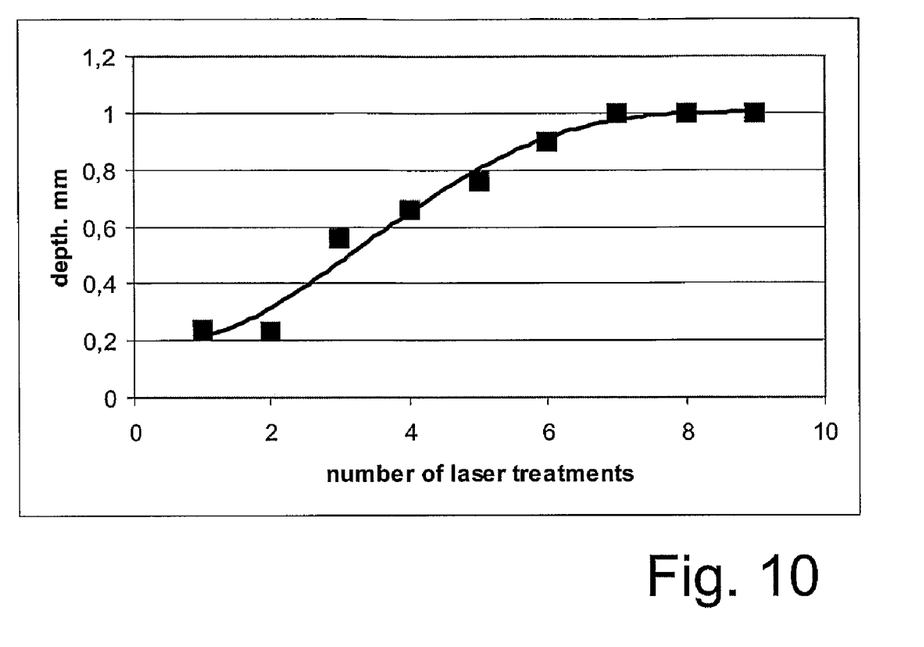
FIG. 10 is a graph showing the depth of indentation in an adhesive material upon repeated laser treatments for a skin plate product in accordance with the present invention.

FIG. 10 shows that the depth of indentation in an adhesive material is increased by repeating the laser treatment a number of times. The figure shows how the depth increases with the number of treatments, notice that a depth of 1 mm means that a 5×10 mm$^2$ hole has been made in the matrix material. See example 9 for details.

EXAMPLES

Example 1

Circular holes were made having a cylindrical or conical shape or a slanting angle towards the surface with a base diameter (largest diameter) of 1.4 mm and a surface coverage of 20-30%.

Holes were drilled in 0.5 and 1 mm thick adhesive sheets using a continuous power $CO_2$ laser equipped with galvanometric-scanner mirrors. Circular holes were made by a spiral movement of an approximately 200 micron sized laser spot moved at a speed of 80 mm/s and an average power of 15 W. Other shapes of holes were made in a similar manner, simply by reprogramming the movement of the laser spot.

The holes formed in the first matrix-forming material can be filled with two different materials e.g. by applying the second material on the surface of the matrix material and thereafter pressing the material into the holes e.g. using a doctor blade or rolling a cylinder over the surface. This process can be repeated several times as required.

In some cases a final surface treatment such as rolling, heating or other can be applied to the skin plate product to improve surface finish and cohesion of the materials.

Example 2

Holes were also made using a hot air technology where 0.5 mm thick adhesive sheets were placed on top of a mask made of a liner or film having holes of the desired shape and a melting temperature higher than that of the adhesive. The adhesive were then heated in a conventional oven or otherwise to make the adhesive plastic and flow after which holes were made using a hot pressurized air stream applied from the film/liner side. Alternatively, holes were made by suction through mask applying a vacuum on the mask side. In both cases it was found preferable to cool the adhesive by (cool) air immediately after hole formation.

Example 3

Matrix Materials

|  | A | B | C | D |
| --- | --- | --- | --- | --- |
| SIS/SI (Kraton D1107) | 20 | | | |
| SIS/SI (Kraton D119) | | 17 | | |
| SIS/SI (Kraton D1161) | | 6 | | |
| SIS/SI (Quintac 3520) | | 7 | 30 | 30 |
| Resin (Arkon P70) | | 35 | | |
| Resin (Arkon P90) | | | 32 | 33.5 |
| Resin (Arkon P115) | 40 | | | |
| Paraffin oil (PL-500) | 40 | 35 | 32 | 33.5 |
| Citrofol BII | | | 6 | 3 |

Compositions of matrix materials A to D in % of the constituents. SIS/SI is styrene-isoprene-styrene tri-block copolymer with different amounts of styrene-isoprene di-block content. The resins act as tackifiers, Citrofol BII is a plasticiser.

Example 4

Hole Materials

|  | I | II | III | IV |
| --- | --- | --- | --- | --- |
| SIS/SI (Kraton D1161) | 25 | 25 | 11.8 | 25 |
| DP209 | 50 | 30 | 23.6 | |
| Paraffin oil (PL-500) | | 20 | 47.1 | |
| TXIB | 25 | 25 | 17.5 | 25 |
| PL-500 | | | | 20 |
| Blanose | | | | 30 |

Compositions of hole materials I, II and III in % of the constituents prepared as described in WO02066087. SIS/SI is styrene-isoprene-styrene tri-block copolymer, DP209 is a 40% w/w dispersion of cross-linked polyacrylic acid based copolymer in mineral oil (DP209-9314 from Ciba Specialty Chemicals) and TXIB is a plasticiser from Eastman.

Example 5

Laser Drilled Holes

Holes are drilled in 0.3 to 1 mm thick adhesive sheets using a conventional continuous power $CO_2$ laser equipped with galvanometric-scanner mirrors and a f=300 mm meniscus lens (Allprint Smart 50 from Allec). Movement of the laser beam is controlled using the ALLPRINT Smart Job software, the shape of drilled features is controlled by adjusting the laser marking parameters given in the table below to suit the material of choice. Most laser-marking software provide similar features to those listed in the table.

| Laser marking parameter | value |
| --- | --- |
| Power | The laser power |
| Mark velocity | Velocity of laser spot with the laser turned on |
| Jump velocity | Velocity of laser spot with the laser turned off |
| Jump delay | Break time after each jump |
| Mark delay | Break time at the end of each laser stroke |
| On delay | The time between starting of the galvo mirrors at the beginning of the stroke and turn-on of the laser beam |
| Off delay | The time between stopping of the galvo mirrors at the end of the stroke and turn-off of the laser beam |

Laser marking parameters used to control the shape of drilled features. The parameters must be optimised to each individual material.

Example 6

Holes Made Using Hot Air

Holes are made using standard hot-air technology where 0.2-0.8 mm thick adhesive sheets are placed on top of a mask made of a liner or film having holes of the desired shape and size. The liner or film can be made of any material having a melting temperature above that of the adhesive, but is preferably a polymer liner (e.g. siliconised PE or PET) commonly used in adhesive processing.

The adhesive is then heated in a conventional oven or by other means to make the adhesive plastic and flow. The holes are made using either a hot pressurised air stream applied from the film/liner side or by suction through the mask using a vacuum applied at the film/liner side. Finally, the adhesive is cooled by air after hole formation.

Example 7

1 mm thick adhesive sheets are made by thermoforming matrix material D between two PE liners. Holes are laser drilled in the adhesive sheets through the liner using spiral movement of the laser beam and the following parameters:

| Laser marking parameter | Value |
| --- | --- |
| Power | 50 W |
| Mark velocity | 150 mm/s |
| Jump velocity | 20000 mm/s |
| Jump delay | 0 µs |
| Mark delay | 30 µs |
| On delay | 0 µs |
| Off delay | 250 µs |

The holes are conical in shape, the slanting angle α (see FIG. 4) is approximately 110°. The largest diameter is 1.5 mm and approximately 20% of the top surface is covered with holes.

The holes are filled through the perforated liner with hole material II using a doctor blade or a rolling cylinder utilising the relative low viscosity of the hole material compared to the matrix material.

Finally, the perforated liners are replaced by suitable "fresh" liners.

Example 8

Varying Hole Shape Through Laser Drilling 1 mm thick adhesive sheets are made by thermoforming matrix material B between two PE liners. Holes are laser drilled in the adhesive sheets through the liner using spiral movement of the laser beam, varying either the power or the mark velocity, other parameters are:

| Laser marking parameter | Value |
| --- | --- |
| Power | 20 W |
| Mark velocity | 150 mm/s |
| Jump velocity | 20000 mm/s |
| Jump delay | 0 μs |
| Mark delay | 30 μs |
| On delay | 0 μs |
| Off delay | 250 μs |

The holes are conical in shape, the largest diameter is 4 mm and the angle alpha (α) is varied by tuning the laser power or the mark velocity as shown in the FIGS. 8 and 9.

The holes are filled through the perforated liner with hole material I, II or IV using a doctor blade or a rolling cylinder utilising the relative low viscosity of the hole materials compared to the matrix material.

Finally, the perforated liners are replaced by suitable "fresh" liners.

Example 9

Varying Hole Depth Through Laser Drilling 1 mm thick adhesive sheets are made by thermoforming matrix material B between two PE liners. A laser treatment consisting of 10 parallel lines with a spacing of 0.5 mm and a length of 10 mm creates a 5×10 mm² rectangular hole in the liner and a corresponding 5×10 mm² indentation into the material. Laser treatment are made through the liner using the parameters:

| Laser marking parameter | Value |
| --- | --- |
| Power | 20 W |
| Mark velocity | 150 mm/s |
| Jump velocity | 20000 mm/s |
| Jump delay | 0 μs |
| Mark delay | 30 μs |
| On delay | 0 μs |
| Off delay | 250 μs |

The depth of the indentation is increased by repeating the laser treatment a number of times. FIG. 10 shows how the depth increases with the number of treatments, notice that a depth of 1 mm means that a 5×10 mm² hole has been made in the matrix material.

Example 10

An adhesive construction as in example 7 is made using matrix materials A or C and the laser parameters:

| Laser marking parameter | Value |
| --- | --- |
| Power | 50 W |
| Mark velocity | 150 mm/s |
| Jump velocity | 20000 mm/s |
| Jump delay | 0 μs |
| Mark delay | 30 μs |
| On delay | 0 μs |
| Off delay | 250 μs |

Conically shaped holes are obtained with α≈100° or α≈110° in the case of matrix materials A or C respectively. The holes are filled with hole materials I, II or IV as described above.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. An adhesive with a top surface and a bottom surface comprising a first matrix-forming material and a second material, the second material being different from the first matrix-forming material and being placed in zones within the first matrix-forming material, at least one of said zones of the second material extending from the top surface to the bottom surface of the adhesive to form an exposed area of said second material on said top surface and an exposed area of said second material on said bottom surface, said exposed area of the second material at the top surface of the adhesive having a different pattern than said exposed area of the second material at the bottom surface of the adhesive, said zones of the second material being in the form of bodies of frustum of cones with a basis of said bodies of frustum of cones being at a same surface, said exposed area of the second material at one of the top and bottom surfaces having a different size than the exposed area of the second material at the other of said top and bottom surfaces, said different sizes of the exposed areas and said exposed areas being formed by said second material in the form of the bodies of frustum of cones with the basis thereof being at the same surface causing said second material to have a bigger effect on one side of the adhesive than on the other side thereof.

2. The adhesive according to claim 1, wherein the exposed area of the second material at the top surface of the adhesive is larger than the exposed area of the second material at the bottom surface of the adhesive.

3. The adhesive according to claim 1, wherein a distribution of the exposed area of the second material at the top surface of the adhesive is different from a distribution of the exposed area of the second material at the bottom surface of the material.

4. The adhesive according to claim 1, wherein a density of the exposed area of the second material at the top surface of the adhesive is different from a density of the exposed area of the second material at the bottom surface of the material.

5. The adhesive according to claim 1, wherein areas of at least two neighboring zones at one of the surfaces are sufficiently large to be interconnected.

6. The adhesive according to claim 1, wherein at least one of the materials is a skin-friendly self-adhesive material.

7. The adhesive according to claim 1, wherein the zone with the second material is in the form of cylindrical bodies having slanting axes in relation to planes of the first and second surfaces and wherein at least one of the cylindrical bodies has a length insufficient to reach from one surface to the other surface.

8. The adhesive according to claim 1, wherein at least one of the zones with the second material is constituted by units of at least two second materials.

9. The adhesive according to claim 1, wherein at least one of the zones with the second material is not completely filled.

10. The adhesive according to claim 1, wherein the zone with the second material is manufactured by providing holes in the first material and then filling the holes with the second material.

11. The adhesive according to claim 10, wherein the zone with the second material is cut with a laser and subsequently filled.

12. The adhesive according to claim 1, in combination with an ostomy appliance, said adhesive being a part of or all of an adhesive wafer for adhering said ostomy appliance to the skin.

13. The adhesive according to claim 1, in combination with a wound dressing, said adhesive being a part of or all of an adhesive surface for adhering said wound dressing to the skin.

14. The adhesive according to claim 1, wherein said different sizes of the exposed areas of the second material configure said adhesive to have different peeling forces in different directions to help prevent unintended removal of the adhesive from skin.

15. The adhesive according to claim 1, wherein a plurality of the zones of the second material extend from the top surface to the bottom surface to form the exposed areas on the top and bottom surfaces.

16. A skin plate product having a first and a second surface comprising a first matrix-forming material provided with a number of holes extending from at least one surface of the product, said holes containing at least one second material which is different from the matrix-forming material and at least one of the materials being a skin-friendly adhesive material, a plurality of the holes extending from the first to the second surface to form exposed areas of the second material on the first and second surfaces corresponding to the holes that are differently distributed, said holes of the second material being in the form of tapered bodies each having a larger end and a smaller end, all of said tapered bodies having a same orientation with all of said larger ends being at a same surface of said product such that said exposed area of the second material at one of the to and bottom surfaces is larger than the exposed area of the second material at the other of said top and bottom surfaces, said product having different adhesive properties on the to surface as compared with the bottom surfaces due to said different sizes of the exposed areas and said exposed areas being formed by said tapered bodies of said second material.

17. The skin plate product according to claim 16, wherein all of the holes containing the second material extend through an entire thickness of the product and wherein boundary surfaces between the holes and the first matrix-forming material are in the form of surfaces which intersect the first and second surfaces in varying slanting angles.

18. A skin plate product having a first surface and a second surface comprising a first matrix-forming material provided with a number of holes extending from at least one surface of the product, said holes containing at least one second material which is different from the matrix-forming material, at least one of the materials being a skin-friendly adhesive material, a plurality of the holes extending from the first surface to the second surface and areas of the first and second surfaces corresponding to at least one of the holes being of different sizes, said holes of the second material being in the form of bodies of frustum of cones with a basis of said bodies of frustum of cones being at a same surface so that an exposed area of the second material at one of the top and bottom surfaces has a different size than an exposed area of the second material at the other of said to and bottom surfaces, one side of said product having different adhesive properties than the other side thereof due to said different sizes of the exposed areas and said exposed areas being formed by said second material in the form of the bodies of frustum of cones with the basis thereof being at the same surface.

19. A method of producing a skin plate product having a first surface and a second surface and having a first matrix-forming material provided with a number of holes extending from at least one surface of the product, said holes containing at least one second material which is different from the matrix-forming material and at least one of the materials being a skin-friendly adhesive material, said holes of the second material being in the form of bodies of frustum of cones with a basis of said bodies of frustum of cones being at a same surface so that an exposed area of the second material at one of the top and bottom surfaces has a different size than an exposed area of the second material at the other of said to and bottom surfaces, said different sizes of the exposed areas and said exposed areas being formed by said second material in the form of the bodies of frustum of cones with the basis thereof being at the same surface causing said second material to have a bigger effect on one side of the adhesive than on the other side thereof, and at least one of said holes extending from a top surface to a bottom surface of the product, comprising the steps of:
  a) providing a first matrix-forming material;
  b) forming holes in the first matrix-forming material by removing material corresponding to a desired pattern of the second material; and
  c) providing a source of at least second material and dispensing said second material into the holes provided by removing the first matrix-forming material in step b).

20. The method according to claim 19, wherein the first matrix-forming material is a continuous source of a skin-friendly material.

21. The method according to claim 19, wherein the first matrix-forming material being removed in step b) is removed using radiation technology.

22. The method according to claim 21, wherein the first material being removed in step b) is removed using laser technology.

* * * * *